United States Patent [19]
Klein et al.

[11] 4,118,127
[45] Oct. 3, 1978

[54] METHOD OF DETECTING FAULTS IN MOVING WEBS OF MATERIALS

[75] Inventors: Hans-Joachim Klein, Wuppertal; Manfred Rupprecht; Heinz Wonneberg, both of Leverkusen; Julius Geiger, Odenthal-Gloebusch; Günter Masa, Leverkusen, all of Germany

[73] Assignee: AGFA-Gevaert Aktiengesellschaft, Leverkusen, Germany

[21] Appl. No.: 777,334

[22] Filed: Mar. 14, 1977

[30] Foreign Application Priority Data

Mar. 18, 1976 [DE] Fed. Rep. of Germany ....... 2611539

[51] Int. Cl.$^2$ ............................................. G01N 21/32
[52] U.S. Cl. .................................... 356/200; 250/563; 250/572; 356/237
[58] Field of Search ............... 356/199, 200, 237, 238; 250/562, 563, 572

[56] References Cited

U.S. PATENT DOCUMENTS

| | | | |
|---|---|---|---|
| 3,510,664 | 5/1970 | Nichols | 250/563 |
| 3,812,373 | 5/1974 | Hosoe et al. | 356/200 |
| 3,972,624 | 8/1976 | Klein et al. | 356/200 |
| 4,011,457 | 3/1977 | Wolf | 356/200 |

Primary Examiner—John K. Corbin
Assistant Examiner—R. A. Rosenberger
Attorney, Agent, or Firm—Connolly and Hutz

[57] ABSTRACT

A web of paper or foil to be investigated is optically scanned line by line transversely to its direction of movement by a stationary scanning device and read off in reflection. The length of scanning line is greater than or equal to the width of the web of material under investigation. At least one time mark is formed electronically within a scanning line, which mark, starting from one end of the scanning range, is shifted forwards by a constant step with each scanning movement until the other end of the scanning range has been reached. The instantaneous value of reflected signal appearing in each case at the time mark is then averaged out over a cycle consisting of several scanning movements. A fault is only indicated if there is a deviation from the average value.

14 Claims, 8 Drawing Figures

METHOD OF DETECTING FAULTS IN MOVING WEBS OF MATERIALS

This invention relates to a method of detecting faults and for identifying and localising longitudinally orientated faults in moving webs of paper or foil, in particular photographic materials. In this method, the web is optically scanned line by line transversely to its direction of movement by a stationary scanning device whose length of scanning line is greater than or equal to the width of the web of material under investigation, and the signals produced by scanning are picked up as reflected light. The instantaneous values of the reflection of the scanning signal emitted from the scanning device are averaged. A fault is indicated only if a deviation from the average value occurs.

In the manufacture of webs of material faults may occur in the web which may seriously impair the subsequent use of the webs. This is particularly so in the case of coated sheets such as photographic films and papers, where faults may occur especially in the layers applied to a support. Apart from faults in the form of spots, such as specks of dirt and bubbles, the most serious faults are elongated faults extending in the longitudinal direction of the web, such as casting stripes or scratches, which may frequently extend over the whole length of the web and thus substantially reduce its quality. It is imperative that such faults which extend in the longitudinal direction of the web be detected.

The known optical methods for detecting faults in moving webs of materials is a disadvantage. The light reflected or transmitted from the web and received by the photodetector is modulated by the properties of the material of the web even where there are no faults since even a fault-free web is not necessarily completely uniform. The signal produced in the photo-detector therefore has a certain irregularity (background noise) even in the absence of faults.

In most cases, the background noise is cut out electronically by amplitude threshold devices (e.g. Schmitt-Triggers or limiter diodes) so that faults are detected in the web of material only the electric pulses they produce are greater than the maximum noise pulses and therefore greater than the threshold voltage. Some improvement is obtained by a method in which a modified output signal of the photodetector is formed which is characteristic of the peak noise averaged over a period of time, and this output signal is compared with the original output signal of the photodetector by means of a voltage comparator so that unwanted noise components are suppressed and the comparator delivers an output signal only in the presence of a pulse produced by a genuine fault. In order to reduce the false alarm signals even further in faulty material, the output signal of the comparator may in addition be fed into a discriminator with a constant threshold voltage (U.S. Pat. No. 3,510,664). Additional frequency discriminating methods using filters to separate pulses due to faults in the material from background noise (e.g. U.S. Pat. Nos. 3,510,664 and 3,206,606) do not provide an optimum solution since there is generally very little difference in frequency between pulses produced by faults and background noise. Such arrangements serve merely to filter out noise frequencies which do not fall within the range of measured frequencies.

A method for the detection of faults and identification and localisation of longitudinally orientated faults on moving webs of material has recently been described (U.S. Pa. No. 3,972,624) in which an optical scanner is so operated that the position of the scanning line is reciprocated parallel to itself and transversely to the longitudinal direction of the web. Two clearly defined time marks are produced in the scanning line so that the web of material can be scanned in sequence at these marks while the scanning period is reciprocated over the whole web at constant velocity. The background noise is eliminated by continuous formation of the average value of the signal produced by the web at each time mark and modulated by the surface property of the web. In this way it is possible to detect even very fine longitudinal faults which have amplitudes equal to or even smaller than the background noise amplitudes.

This method was conceived for scanning relatively wide webs of material and has proved to be very satisfactory for this purpose. However, for scanning relatively narrow webs (particularly if the width of the web is less than the length of the scanning line) the mechanical expenditure required for the reciprocating motion is excessive.

According to the invention there is provided a method for the detection, identification and localisation of longitudinally orientated faults in a moving web in which the web is optically scanned line by line transversely to its direction of movement by a stationary scanning device and read off in reflection, the length of scanning line of the scanning device being greater than or equal to the width of the said web, wherein at least one time mark is formed electronically within the scanning line, which mark, starting from one end of the scanning range, is shifted forwards equal steps with each scanning movement until the other end of the scanning range is reached, and the instantaneous value of reflected scanning signal appearing at the time mark is summed, over a scanning cycle consisting of a plurality of scanning movements and a fault is indicated only when there is a deviation from a predetermined value.

The width of the step and hence the total number of steps within the scanning range is preferably adjustable.

A preferred embodiment of the invention is characterised in that the time mark is produced by the L-O flank of a pulse which, starting from a line starting pulse, is triggered by a time element, the lengths of the pulses increasing by $T_2$ from one scanning line to the next.

The invention has the advantages of greater operational reliability compared to that described in U.K. Patent Application No. 54,602/74 since the mechanical traverse motion of the measuring head is eliminated.

Another important advantage is that the faults are more easily localized. The principle of measuring the moving time marks enables the fault to be localised in relation to the width of the web without the web having to be subdivided into numerous fixed measuring channels situated side by side. This localisation in relation to the width of the web means that the position of a longitudinal fault within the width of the web is known independently of the position of the web relative to the scanning device since the first passage of the time mark across the fault determines the next following passage of the time mark which in turn determines afresh the next following passage. The electronic circuit required for this is much simpler than that required when the width is subdivided into channels as mentioned above.

An embodiment of the invention will now be described in more detail with reference to the accompanying drawings. In particular, the arrangement and mode of operation of the corresponding circuit is explained.

FIG. 5b is a pulse time diagram corresponding to FIG. 5a; and

Figure 1:
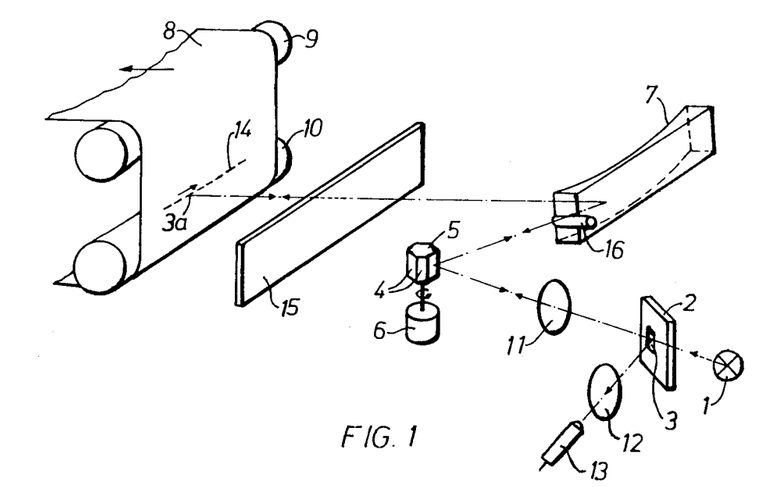
FIG. 1 is a schematic diagram of the optical reflection scanner.

FIG. 1 is a simplified, schematic perspective view showing one example of the optical scanner. Light from a tungsten lamp 1 passes through a semi-transparent mirror 2 arranged at an angle of e.g. 45° to the incident light to illuminate an inlet gap 3 which is adjustable in height and width and fixed to the back of the mirror 2, on the side remote from the lamp 1.

A mirror wheel 5 covered from plane mirrors 4 and driven by a motor 6 is rotatable so that when the wheel rotates its periphery, i.e., the mirrors 4, moves in the focus of a parabolic mirror 7 arranged parallel to a web of material 8 which moves in the direction indicated by the arrow. To ensure that the web 8 will move steadily it is passed over two rollers 9 and 10 which are placed close together and over which the web is wrapped with as large a looping angle as possible.

A convex lens 11 focuses the light from the gap 3 on to the mirrors 4 of the mirror wheel 5, which reflect the light on to the parabolic mirror surface 7 which in turn projects it as a small scanning spot 3a on to the web of material 8, the light being incident on the surface of the web in a direction perpendicular thereto. Since the mirror wheel is situated below the parabolic mirror 7, the wheel 5 and mirror 7 are set at a slight angle to each other for purposes of reflection and focusing. The light reflected by the web 8 and modulated by the surface properties of the web retraces its path to return to the semi-transparent mirror 2 by way of the parabolic mirror 7, mirrors 4 and lens 11. It is then deflected by reflection from the mirror 2 and focused by a lens 12 on to a photoelectric receiver 13 which may be, for example, a rapid, highly sensitive and as far as possible low noise photoelectric diode or phototransistor. the scanner thus operates on the principle of autocollimation.

When the mirror wheel 5 rotates in the sense indicated, the beam reflected by the parabolic mirror 7 shifts parallel to itself in the direction indicated so that the scanning spot 3a scans the web 8 along a scanning line 14. The system is so arranged that only one mirror 4 of the mirror wheel 5 is used for each scanning operation. If the web 8 moves in the direction of the arrow, it is therefore scanned line by line without any gaps along the length of the scanning line 14.

Any faults on the web of material are detected by the scanning spot 3a and transmitted via the parabolic mirror 7, mirror wheel 5, lens 11, semi-transparent deflecting mirror 2 and lens 12 to the photoelectric detector 13 which converts them into electric fault pulses. If the system is used to check photographic material, an infrared filter 15 which absorbs light in the visible spectrum is arranged between the parabolic mirror 7 and web 8. The scanning beam produces pulses at the ends of the parabolic mirror 7 as it enters and leaves the mirror, but these pulses do not interfere with the process. Laterally to the parabolic mirror, another photoelectric diode 16 is arranged within the path of the scanning beam so that it is swept by the beam and delivers a line starting pluse before the beginning of each scanning movement. This line starting pulse could equally well be produced by some other means, for example by inductive scanning of the mirror wheel. In the example given here, in which the spot scans over a width of 7 cm, which is the length of the scanning line 14, the speed of rotation of the mirror wheel is 50 revs/sec. If the number of mirrors 4 is 16, the scanning fequency is 800 cycles per second and the total time of one movement of a mirror 4, that is to say the sum of the actual scanning time $T_a$ on the web 8 and a certain dark time $T_d$ between two mirror movements, which depends on the geometry and number of mirrors, is T = 1.25 ms. If the rate of movement of the web is 40 m/min, for example, the web 8 is moved forward during this time (1.25 ms) by 0.83 mm.

Figure 2:
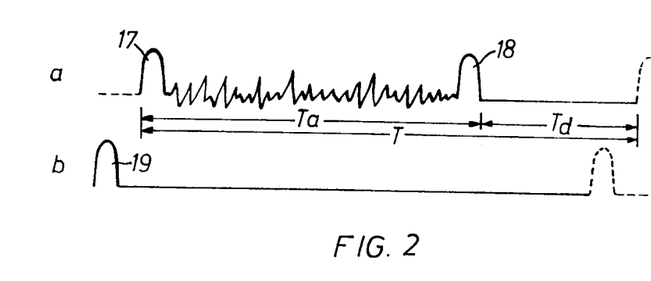
FIG. 2 shows the signal for a line scanning received by the photoelectric receiver and the corresponding line starting pulse.

FIG. 2a shows the signal received by the photoelectric receiver 13 when line scanning a web which is free from faults. The signal is then modulated only by the normal surface properties of the web. The web is scanned from left to right. 17 is therefore the entry pulse which is dependent upon the surface of the web and 18 is the associated exit impulse. T = 1.25 ms is the total operational time of a mirror, which is composed of the scanning time $T_a$ and dark time $T_d$.

FIG. 2b shows the corresponding line starting pulse 19 received by the photoelectric diode 16, which occurs before each line scanning movement.

Figure 3A:
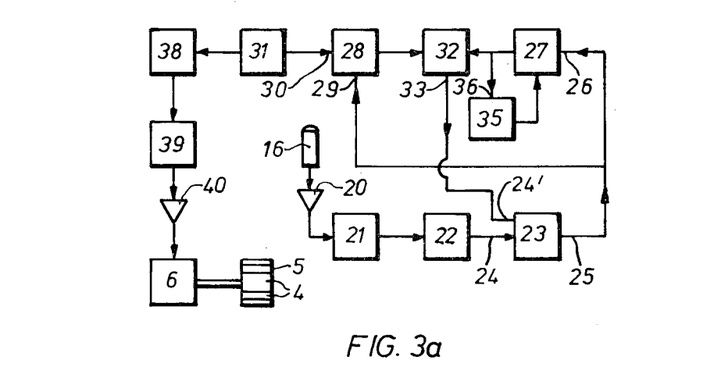
FIG. 3a is a block circuit diagram of an electronic circuit for shifting the time marks.
Figure 3B:
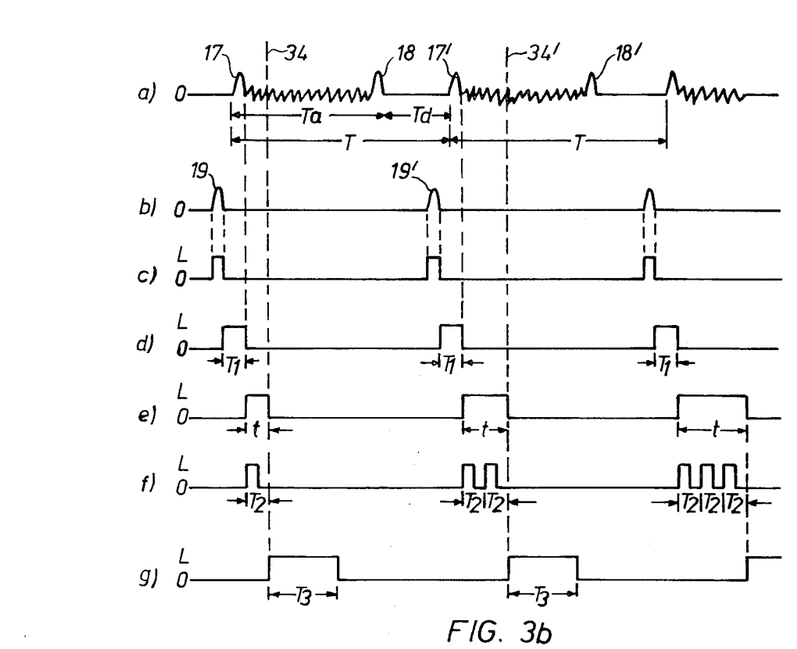
FIG. 3b is a pulse-time diagram corresponding to FIG. 3a for two successive lines of the optical scanner.

FIG. 3a is a block diagram of a circuit for shifting the time mark or marks produced for each scanning line and FIG. 3b is the corresponding pulse time diagram for two successive line scanning movements of the scanner (FIG. 1 and FIG. 2). To enable the operation of the electronic circuit to be more easily understood, FIGS. 3a and 3b will be considered together.

Trace a in FIG. 3b shows the variation with time of the signal for two successive scanning movements received by the photoelectric receiver 13 (FIG. 1) and already amplified, 17 represents the entry pulse already mentioned above and 18 the exit pulse for the first scanning line, 17' and 18' the corresponding pulses for the following scanning movement and T = 1.25 ms is the total time of movement of one mirror.

The line starting pulse produced by the photoelectric diode 16 (FIG. 3a) before the beginning of each scanning line is amplified in the amplifier 20 and transformed into a positive rectangular pulse by the Schmitt-Trigger 21. Trace b in FIG. 3b shows the variation with time of the line starting pulses 19 and 19' respectively for the following scanning line, and trace c in FIG. 3b shows the standardised rectangular pulse derived from it at the output end of the Schmitt-Trigger 21. Connected in series with the trigger 21 is a monostable multivibrator 22 which, starting from the L-O flank of the Schmitt-Trigger 21, transmits another positive rectangular pulse of predetermined width $T_1$ (trace d in FIG. 3b), the L-O flank of which occurs later in time than the entry pulse 17 or 17' which is formed in dependence upon the surface of the web of material (trace a in FIG. 3b) so that the said L-O flank represents the beginning of the permissible scanning range of the scanner. The entry pulse which would interfere with the scanning process is thus suppressed. The time $T_1$ of the monostable multivibrator is adjusted according to the width of the band of material which is required to be scanned. This band should be situated symmetrically between the entry pulses 17 and 17' and symmetrically between the exit pulses 18 and 18'. The time of the monostable multivibrator and hence the beginning of the permissible scanning range of the scanner can be shifted in known manner within the scanning line as desired by altering the time constants of the monostable multivibrator. The end of the scanning range of the scanner and hence the width of material to be scanned are fixed by a step preselector counter 35 which is described below. The L-O flank of the positive rectangular pulse at the output end of the monostable multivibrator 22 activates an RS flip-flop 23 and sets its output 25 at a positive (L) potential by way of its S-input 24 (trace e in FIG. 3b). This O-L flank counts one bit into the counter 27 by way of the input 26 (so that the contents of the counter are now 1 if starting from zero, for example) and at the same time another counter 28 is enabled to count by way of a control input 29. The clock input 30 of the counter 28 is continuously fed with a frequency of $\nu_2 = 1/T_2 = 819200$ Hz from a clock 31, in this example a rectangular pulse generator. However, the counter 28 cannot receive these pulses until the positive signal from the flip-flop 23 has arrived at its input 29. As soon as this L-signal disappears from the input, the counter is no longer enabled to count and is set to zero. The contents of the counters 27 and 28 are fed into a comparator 32 which produces a signal at its output end when the contents of the counters 27 and 28 are equal. This signal returns the output 25 of the flip-flop 23 to zero by way of its R-input 24', i.e., the contents of the counter 28 are cancelled by way of the input 29. The line starting pulse 19' of the next following line (trace b in FIG. 3b) delivers another L-O flank to set the flip-flop 23, by way of the amplifier 20, Schmitt-Trigger 21 and monostable time element 22 in the same way as described above. The O-L flank formed at the flip-flop output now counts another bit into the counter 27 the contents of which are now equal to 2 and enables the counter 28 to count. The counter 28 must now count from 0 to 2 before the comparator determines that the contents of the counters 28 and 27 are equal. This equal signal returns the flip-flop 23 to its starting position, i.e., O-potential at the output 25. The time t of the output signal of the flip-flop 23, i.e., the time during which the output 25 is at L-potential is thus variable and is increased by $T_2$ from one scanning line to the next (cf traces e and f in FIG. 3b). One thus obtains the relationship $t = n T_2$ where n is the number of scanning lines. The L-O flank of the flip-flop 23 thus moves by a step $T_2$ from one scanning line to the next over the permissible scanning range of the scanner, the beginning of the range being determined by the O-L flank of the flip-flop 23, as described above (traces e and a in FIG. 3b). The time mark or scanning mark 34 or 34' for the next scanning line, i.e., the moment in time when the signal at the scanner is interrogated, is defined by the L-O flank of the flip-flop 23 (trace e in FIG. 3b). The time mark 34 is thus shifted by steps of $T_2$ per scanning line while the scanner scars linearly. The scanner signal (trace a in FIG. 3b) is thus interrogated at the time mark which travels over the scanning range. The end of the scanning range is determined by the number n of steps and this number n is selected in the step preselector 35. When the counter 27 which is connected to the input 36 of the step preselector 35 has reached the predetermined number of steps n, the end of the measuring range over which the time mark is shifted has also been reached and the counter 27 is set to zero by way of the input 37 so that the process of shifting the time mark can begin from the beginning.

The process will now be explained with the aid of a numerical example. In an optical scanner having a scanning velocity on the web of material of e.g. $V = 65.6$ m/s $= 0.0656$ mm/µs, a clock frequency is used, as given in the example, of $\nu_2 = 1/T_2 = 819200$ Hz, so that $T_2 = 1/\nu_2 = 1/819200 = 1.22 \times 10^{-6}$s $= 1.22$ µs. The local shift $\chi$, based on the range of measurement, of the time marks 34 and 34' from one scanning line to the next is given by $x = VT_2 = 1.22 \times 0.0656$ mm $= 0.08$ mm. With a step preselection of $n = 500$, it is possible to scan a width of web $b = n\chi = 500 \times 0.08$ mm $= 40$ mm. At a given scanning velocity V and clock time $T_2$, the scanning range of the band of material can therefore be determined by the step preselection value n. Since the shift in the time mark by the amount x takes place from line to line, that is to say in each case after the scanning time $T = 1.25$ ms, the time for shifting the time mark over the scanning range is obtained from the relationship $n T = 500 \times 1.25 = 625$ ms $= 0.625$ s. This numerical example has been chosen arbitrarily. With suitable choice and combination of the individual parameters, the individual step x can easily be made smaller and hence the resolution of signal detection greater, for example by increasing the step number n for a given scanning range. As can be seen from the numerical example, the size of the step x of the time mark from one scanning line to the next depends on the scanning velocity V of the scanner, i.e., on the speed of rotation of the drive motor of the scanner, and the clock frequency $\nu_2 = 1/T_2$.

Although synchronisation of the motor with the clock frequency is not necessary when using synchronous motors, it does increase the functional reliability of the process. Such synchronisation may, for example, be carried out as follows (referring to FIG. 3a). The frequency of the rectangular pulses produced by the clock 31 is reduced to 50 Hz by a frequency divider 38. A low pass filter 39 connected to the frequency divider produces a sinusoidal voltage by filtering out the harmonic overtones, and this sinusoidal voltage drives the synchronous motor of the scanner by way of an output amplifier 40. Synchronisation can also be achieved with any other type of motor in known manner and it can also be carried out in reverse by synchronising the clock using a signal transmitter attached to the motor.

Figure 4:
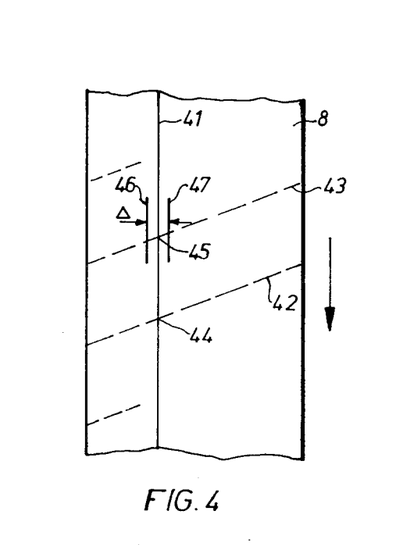
FIG. 4 illustrates the principle according to which a longitudinal fault is localised within the width of the band.

Identification of a fault as a longitudinal fault can also be achieved with only one scanning mark if the fault found in the course of the displacement of the scanning mark over the measuring range is fed in as information related to the width of the web and the system is then tested to see whether during the next passage of the scanning mark the fault again occurs in the same position within a given tolerance. This is illustrated in FIG. 4 which shows a longitudinal fault 41 on a web of material 8 moving in the direction indicated by the arrow. The time mark 34 moving for example from left to right over the width of the web (FIG. 3b) describes a path 42 relative to the moving web during the first passage and the path 43 during the next passage. It must now be tested whether the fault recognised at the point 44 during the first passage is to be found at the corresponding point 45 in relation to the width of the web during the second passage within a tolerance Δ relating to the width of the web, as characterised by the two lines 46 and 47.

Figure 5A:
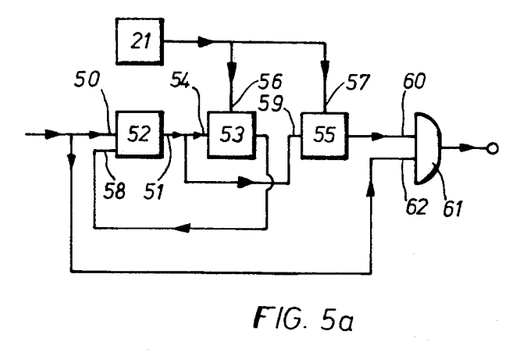
FIG. 5a is the block circuit diagram for testing the position of a longitudinal fault within the width of the band.
Figure 5B:
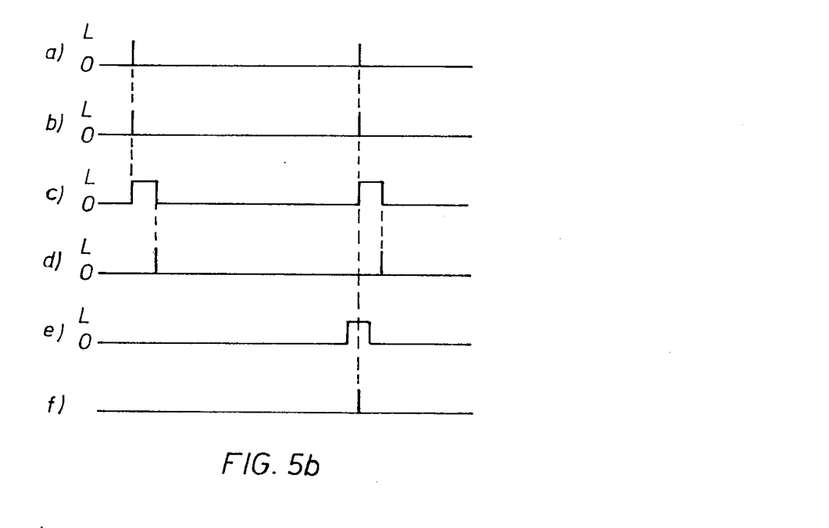

FIG. 5a shows one example of a circuit for carrying out this test. FIG. 5b shows the corresponding pulsetime diagram for two successive passages of the time mark. To enable these figures to be more clearly understood, they will be considered together.

As shown by FIG. 4, the time mark passed through and recognised the fault 41 at the point 44 in its first passage 42. This point in time is represented by 48 in trace a of FIG. 5b and the corresponding fault signal by 49 in trace b of FIG. 5b. During the following passage 43 the fault 41 is reecognised at point 45. This corresponds to point in time 48' in trace a of FIG. 5b. The corresponding fault signal 49' is shown in trace b of FIG. 5b. The fault signal 49 sets an output 51 of a flip-flop 52 (FIG. 5a) at L-potential (trace c in FIG. 5b) by way of an input 50. As a result, both a preselector counter 53 which determines the tolerance Δ by suitable preselection is opened by way of an input 54 and a shift register (55 is opened by way of an input 59. The function of the shift register is to determine the position in relation to the width of the web of the tolerance band Δ determined by the counter 53 so that during the next passage 43 the tolerance band Δ will be situated symmetrically with respect to the fault 41, in other words between the markings 46 and 47. When the counter 53 and the shift register 55 have been opened, the line starting pulses are counted in by the Schmitt-Trigger 21 (FIG. 3a and trace c in FIG. 3b) by way of inputs 56 and 57. When the counter 53 reaches its preselected value Δ, an output pulse is produced at the counter (trace d in FIG. 5b) to reset the flip-flop 52 by way of the input 58 (trace c in FIG. 5b). The shift register 55 is thereby also blocked by the input 59 which is now at zero so that nothing further is fed in but the contents Δ which have so far been fed in are shifted forwards rhythmically by $[n - (\Delta/2)]$ steps by way of the input 57. Since the shift register itself only has a length of $[n - (\Delta/2)]$ bit and the contents amount to Δ steps, the counter begins to overflow after $[n - (3/2)\Delta]$ steps and is terminated after $[n - (\Delta/2)]$ steps. While the counter is overflowing during the tolerance range Δ, an input 60 of an AND-gate 61 is at L-potential (trace e in FIG. 5b) so that only those faults which have been scanned by the scanning mark and which lie within the tolerance Δ in relation to the width of the web (traces a and b in FIG. 5b) produce a signal at the output of the AND-gate 61 by way of its input 62 (trace f in FIG. 5b); in other words only these faults can be detected. These conditions are fulfilled by longitudinal faults.

Since the process described above of relating the position of the fault to the width of the web is constantly begun again from the beginning by the detected fault, in other words there is always only one passage of the measuring mark which is compared with the next following passage, the position can be accurately related to the width of the web. This is an important advantage over the hitherto conventional methods of relating longitudinally orientated faults to the width of the web by means of a fixed sub-division into channels since in the latter case it is always necessary to take into account the adjacent channels on either side.

Figure 6:
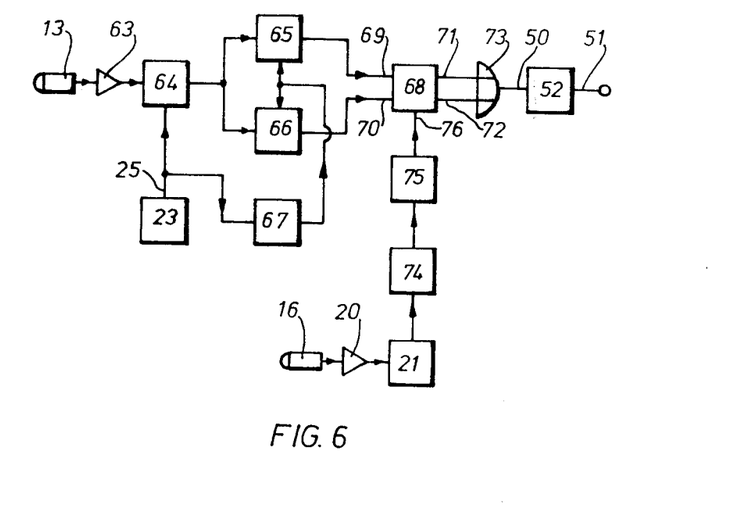
FIG. 6 is a block circuit diagram of the electronic circuit used for evaluating the data for identifying longitudinal faults.

FIG. 6 is a block diagram of an electronic circuit used for interpreting the signals for recognising longitudinal faults. For a clearer understanding of the operation of the electronic circuit, FIGS. 6 and 3b will be considered together. The signal produced by the photoelectric receiver 13 (see also FIG. 1) in response to the reflected beam modulated by the properties of the surface of the web of material is amplified in a broad band amplifier 63 and conducted to the input of a Sample and Hold member 64 which is suitable both for positive and for negative input amplitudes, (e.g. the SHA 1A model manufactured by Analog Devices, USA). The signal obtained at the output end of the amplifier 63 for two successive line scannings of the scanner is represented in trace a in FIG. 3b. The output 25 of the flip-flop 23 (FIG. 3a) is connected to the control input of the sample and hold member 64. When the control input of the sample and hold member 64 is at L-potential, that is to say during the time t (FIG. 3b-e), the sample and hold member is switched to the function "Sample" whereas if the input is at O-potential, it is switched to the function "Hold". This means that the sample and hold member is always switched from sample to hold at the time mark 34 or 34' (FIG. 3b) and is switched to sample at the transition from O to L. The function "Sample" means that the output of the sample and hold member always carries the input signal whereas when the member is switched to "Hold" the signal value which is at the input at that moment in time is maintained at the output as a fixed voltage value for the duration of the hold time. The output of the sample and hold member 64 is connected to two voltage frequency converters 65 and 66, the converter 65 being suitable for positive input signals and the converter 66 for negative input signals. The object of these converters is that during an exactly specified converter time $T_3$ wherein the "Hold" time (of the sample and hold member 64) they must convert the positive or negative value which happens at that time to be at the output of the sample and hold member 64 into a pulse sequence of specified rectangular pulses having a frequency proportional to that value. The converter ratio is 10 kHz/V (e.g. converters of the type W 10-10P or W10-10N, BPS-Electronic GmbH, Hanover).

In the example given, the conversion time $T_3$ for the instantaneous value held at the time mark 34 or 34' and stored in the sample and hold member 64 is selected to be equal to $T_d$ as will be explained below (traces a and g in FIG. 3b).

The output of the monostable multivibrator 67 triggered by the flip-flop 23 with the L-O flank (trace e in FIG. 3b) for producing the conversion time $T_3$ is connected to the trigger inputs of the voltage frequency converters 65 and 66 so that conversion of the prevailing signal will only take place during the conversion time $T_3$ (trace g of FIG. 3b). The conversion time $T_3$ is suitably selected to be equal to $T_d$ in this example because when the time mark 34 or 34' reaches the righthand edge of the scanning range, at least the conversion time $T_3 = T_d$ is available before the time mark begins its next passage at the lefthand edge of the scanning range. For shorter scanning ranges, correspondingly longer conversion times may be selected. The conversion time may, of course, also be produced in some other manner, for example from the clock 31 by fixing a number of pulses. The outputs of the voltage frequency converters 65 and 66 are connected to the inputs of a forward-backward counter 68 in such a manner that the output of the voltage frequency converter 65 is connected to the forward input 69 and the output of the voltage frequency converter 66 to the backward input 70 of the counter 68. The forward-backward counter 68 can be preset to a selected value, e.g. to the number 32. Two outputs of the counter are also preselected, namely the output 71, e.g. to the number 64 and the output 72 to the number 0. This means that when pulses reach the input 69, they are counted "forwards" from the number 32 onwards. When the preselected number 64 is reached, a pulse appears at the output 71. This happens after exactly 32 input pulses. When, on the other hand, pulses reach the backward input 70, they are counted "backwards" starting from the preselected value 32 until the number 0 is reached, again after 32 pulses, and a pulse appears at the output 72. The outputs 71 and 72 of the counter 68 are combined through an OR-gate 73.

The output of the Schmitt-Trigger 21 (see also FIG. 3a) which produces the standardised line starting pulse (see trace c in FIG. 3b) is connected to a pulse divider 74 which reduces the line starting pulses, e.g. by a ratio of 8:1. After every eighth scanning, a signal appears at the output of the divider 74, from which signal a brief rectangular pulse is produced by the monostable multivibrator 75, and this rectangular pulse is transmitted to the presetting input 76 of the counter 68. By this arrangement, the counter 68 is again preset to the number 32 after every 8 line scannings (scanning cycle). When the counter 68 has been preset to 32 by the arrangement described above, the first of the 8 line scannings of the scanning cycle begins again. The operation of the arrangement so far described will now be explained with the aid of an example.

During the first line scanning, suppose the instantaneous signal value of the noise of the web at the time mark 34 is +0.4 Volt, for example. This value remains at the output of the sample and hold member 64 during the "Hold" time and is converted into a pulse sequence in the voltage frequency converter 65 and counted into the forward input 69 of the counter 68 during the conversion time $T_3$ of e.g. 500 μs. At the given conversion ratio of 10 kHz/Volt, this corresponds to a number of pulses of $10^4 \times 0.4 \times 5 \times 10^{-4} = 2$. The counter 68 therefore now has the new value $32 + 2 = 34$. Now let the instantaneous signal value at the time mark 34' in the second line scanning be −1.2 Volt, for example. This value is appropriately converted into a pulse sequence by the voltage frequency converter 66 and also fed into the backward input 70 of the counter 68 during the conversion time $T_3 = 500$ μs so that a number of pulses amounting to $10^4 \times 1.2 \times 5 \times 10^{-4} = 6$ pulses are subtracted (counted backwards) from the value 34 already stored there so that the new value in the counter is now $34 - 6 = 28$. This process is repeated during the following 6 scannings (3 to 8). Thereafter, the counter is preset to the number 32 as described above and a new scanning cycle begins.

Since interrogation at the time mark will always cover different ranges of the web, due both to the movement of the web and to the movement of the time mark over the scanning range, the surface noise of the web represented in trace a in FIG. 3b appears to be statistically distributed so that the surface noise of the web is summed out by the process described above of digital average formation, for example for every 8 scanning movements, constituting a scanning cycle, since neither the preselected number 64 is reached at the output 71 of the counter 68 nor the preselected number 0 at the output 72, in other words no pulse appears at the output of the OR-gate 73.

If, on the other hand, there is a longitudinal fault in the web, a consistent positive or negative pulse always appears within the statistically distributed noise of the web during the scanning movements, and the time mark moves stepwise (length of step x) over this pulse in the course of its passage and the pulse is constantly scanned in a different position. The time required for this when there are 8 scanning movements is $8T = 8 \times 1.25$ ms = 1 ms. In this example, therefore, this is the length of time during which the fault pulse must appear at the time mark during the passage of the time mark (if all 8 scanning movements are used). This requirement will be met even in the case of narrow pulses since the velocity of passage of the time mark is relatively slow, being $V_1 = x/T = 0.08/1.25$ mm/ms = 0.64 mm/10 ms. Since pulses produced by longitudinal faults are uniform pulses, for example being always positive, each scanning is accompanied by voltage frequency conversion in the voltage frequency converter 65 (FIG. 6) so that pulses are counted in only by way of the forward input 69 of the counter 68. The fault pulse is recognised as representing a fault if after 8 scanning movements, starting from the preset counter contents 32, a further 32 pulses are counted in so that the preselected number 64 is reached and consequently a pulse appears at the output 71 of the counter and hence at the output of the OR-gate 73. This happens when the average scanned pulse value during the 8 scannings of the fault pulse is exactly +0.8 Volt since at a conversion ratio in the voltage frequency converter 65 of 10kHz/Volt, a conversion time of $T_3 = 500$ μs and 8 scanning movements, the number of pulses counted into the counter 68 is $10^4 \times 0.8 \times 500 \times 10^{-6} \times 8 = 32$. The amplitude of the fault pulse may be equal to or smaller than the amplitudes of the background noise of the web since the values of this noise have been summed out and therefore do not have any influence on the detection of faults.

The identification of negative longitudinal fault pulses is achieved in analogous manner. In this case, in contrast to the events described above for the recognition of positive faults, the voltage frequency converter 66 which acts on the backward input 70 of the counter 68 comes into operation and the numbers are subtracted from the preset number 32. When the preselected number 0 is reached, a pulse appears at the output 72 and hence at the output of the OR-gate 73.

In order to ensure that only longitudinal faults and not point faults are detected, it is necessary to check whether a fault found during one passage of the time mark is detected during the following passage of the time mark within the given tolerance Δ in relation to the width of the web. For this purpose, the output of the OR-gate 73 is connected to the input 50 of the flip-flop 52 of the circuit already described with reference to FIGS. 5a and 5b for testing the relationship of the position of a longitudinal fault to the width of the web. The figures given in the example for the sake of illustration are arbitrary and may be replaced by any other values suitable for the problem.

The process described above of shifting the time mark over the scanning range can, of course, easily be extended to several marks moving successively over the scanning range at a specified, constant interval, the average value being then obtained separately for each of these marks by the process already described. If a fault is detected at one time mark, to check whether this is a longitudinal fault it is necessary to observe whether the fault appears again at the next time mark following at a constant interval and in the same position in relation to the width of the web within the given tolerance. The use of a plurality of time marks has the additional advantage, particularly for wide materials, and hence large scanning ranges, and materials moving at high velocities, that the velocity of passage of the time marks can be kept low and hence also narrower and shorter longitudinal faults can be reliably detected.

What we claim is:

1. A method for the detection, identification and localisation of longitudinally orientated faults in a moving web in which the web is optically scanned line by line transversely to its direction of movement by a stationary scanning device and read off in reflection, the length of scanning line of the scanning device being greater than or equal to the width of the said web, wherein at least one time mark is formed electronically within the scanning line, which mark, starting from one end of the scanning range, is shifted forwards equal steps with each scanning movement until the other end of the scanning range is reached, and the instantaneous value of reflected scanning signal appearing at the time mark is summed, over a scanning cycle consisting of a plurality of scanning movements and a fault is indicated only when there is a deviation from a predetermined value.

2. A method according to claim 1, wherein the width of the step and hence the total number of steps within the scanning range is adjustable.

3. A method according to claim 1, wherein the time mark is produced by the falling flank of a pulse which, starting from a line starting pulse, is triggered by a time delay member, and the length of the pulse is increased by the said step from one scanning line to the next.

4. A method according to claim 3, wherein a first counter fed from a clock is compared with a second counter whose contents are increased by one bit from one scanning line to the next, and when the contents of the counters are equal a flip-flop is activated which produces the said falling flank of the pulse of increasing length and at the same time the first counter is cleared.

5. A method according to claim 4, wherein the scanning frequency is synchronised with the frequency of the clock.

6. An apparatus according to claim 4, comprising means for synchronising the scanning frequency with the frequency of the said clock.

7. A method according to claim 1 wherein the fault signal detected in the course of shifting the time mark is stored as information related to the width of the web and a test is made electronically to determine whether during the next following passage of the time mark the fault appears again in the same position in the width of the web within a given tolerance.

8. a method according to claim 1 wherein a plurality of time marks succeeding each other at a constant interval is produced within the scanning line and that a summed value is formed separately for each of these time marks and a fault is indicated only when the summed value deviates at two seccessive time marks from a given value corresponding to the background noise.

9. An apparatus for the detection, identification and localisation of longitudinally orientated faults in a moving web, comprising a stationary scanning device for optically scanning the web line by line transversely to its direction of movement by directing a beam on to the web and detecting the beam reflected therefrom, the length of the scanning line being greater than or equal to the width of the said web; means for forming electronically within the scanning line at least one time mark; means for shifting the time mark forwards by equal steps from one end of the scanning range to the other; means for summing the instantaneous values of the reflected beam at the time mark over a scanning cycle consisting of a plurality of scanning movements; and means for indicating a fault only when there is a deviation in the summed value from a predetermined value.

10. An apparatus according to claim 9, wherein the width of the steps and hence the total number of steps within the scanning range is adjustable.

11. An apparatus according to claim 9, wherein the means for producing the time mark comprises a time delay member which is arranged to be triggered by a line starting pulse to produce an output pulse the falling flank of which triggers the production of the time mark, and the means for shifting the time mark comprises means for increasing the length of the said output pulse by an amount equal to one of the said steps from one scanning line to the next.

12. An apparatus according to claim 11, comprising a first counter fed from a clock, a second counter whose contents are increased by one bit from one scanning line to the next, means for comparing the contents of the two counters, a flip-flop arranged to be activated when the contents of the two counters are equal to produce the said falling flank of the said output pulse and means for simultaneously clearing the first counter.

13. An apparatus according to claim 9, comprising means for storing a fault signal detected during one passage of the time mark and means for determining whether during the next following passage of the time mark the fault appears again in the same position in the width of the web within a given tolerance.

14. An apparatus according to claim 9, comprising means for generating a plurality of time marks succeeding each other at a constant interval.

* * * * *